United States Patent [19]

Lee

[11] Patent Number: 5,282,968
[45] Date of Patent: Feb. 1, 1994

[54] PROCESS FOR SEPARATING AND RECOVERING HALOCARBONS FROM MIXTURES THEREOF

[75] Inventor: Kung H. Lee, Chadds Ford, Pa.

[73] Assignee: E. I. Du Pont de Nemours and Company, Wilmington, Del.

[21] Appl. No.: 923,671

[22] Filed: Aug. 3, 1992

[51] Int. Cl.$^5$ .................. B01D 15/00; B01D 61/00
[52] U.S. Cl. .................. 210/640; 210/651; 203/75; 95/16
[58] Field of Search ........... 210/651, 650, 640, 450, 210/653, 654, 500.27; 203/75; 55/16

[56] References Cited

U.S. PATENT DOCUMENTS

| | | | |
|---|---|---|---|
| 3,947,558 | 3/1976 | vanEijl | 423/483 |
| 4,424,067 | 1/1984 | Tarasenko et al. | 55/16 |
| 4,599,096 | 7/1986 | Burr | 55/16 |
| 4,661,296 | 4/1987 | Grote et al. | 260/413 |
| 4,756,835 | 7/1988 | Wilson | 210/651 |
| 4,793,841 | 12/1988 | Burr | 55/16 |
| 4,863,496 | 9/1989 | Ekiner et al. | 55/16 |
| 5,064,447 | 11/1991 | Lee | 55/16 |

FOREIGN PATENT DOCUMENTS

| | | |
|---|---|---|
| 4806 | 1/1988 | Japan . |
| 218215 | 9/1988 | Japan . |

*Primary Examiner*—Robert A. Dawson
*Assistant Examiner*—Ana M. Fortuna
*Attorney, Agent, or Firm*—James E. Shipley

[57] ABSTRACT

A process is disclosed for separating components of an azeotropic or azeotrope-like mixture containing only organic compounds at least one of which compound is a halocarbon comprising contacting said azeotropic or azeotrope-like mixture with a semipermeable membrane to form at least one exit stream having an increased concentration of at least one component and at least one other exit stream having an increased concentration of at least one other component of the azeotropic or azeotrope-like mixture and, thereafter, recovering at least one exit stream.

2 Claims, No Drawings

PROCESS FOR SEPARATING AND RECOVERING HALOCARBONS FROM MIXTURES THEREOF

BACKGROUND OF THE INVENTION

The present invention relates to an improved process for separating the components of an azeotropic or azeotrope-like mixture containing only organic compounds of which at least one compound is a halocarbon wherein it is difficult and/or impractical to separate the azeotropic or azeotrope-like mixture by conventional means. More specifically, the present invention relates to separating the components of such azeotropic or azeotrope-like mixture by contacting the mixture with a semipermeable membrane to form at least one exit stream having an increased concentration of at least one component and at least one other exit stream having an increased concentration of at least one other component. The exit streams from the contacting step may, thereafter, be recycled for contact with the semipermeable membrane or further processed by conventional means to achieve additional separation and/or recovery of a desired component.

It is well known that halocarbons of commercial interest including chlorofluorocarbons (CFC's), hydrogen-containing chlorofluorocarbons (HCFC's), hydrogen-containing fluorocarbons (HFC's) and perfluorocarbons (FC's) can be manufactured by processes involving halogen exchange reactions wherein a halocarbon which contains a halogen substituent (most often a chlorine substituent) other than or in addition to a fluorine substituent is reacted with a fluorine-donor compound. The fluorine-donor compound is capable of donating a fluorine atom in halogen exchange reactions such as a metal fluoride or hydrogen fluoride used in the presence of various catalytic compounds. The desired product is obtained together with by-products such as under- or over-fluorinated products, decomposition products, unreacted reactants and the like. The desired product usually must then be separated from these by-products and/or contaminants.

While most separations of this type are carried out readily by well known processes such as distillation, phase separation and the like, some separations present problems which preclude using these processes especially when halocarbons form azeotropic or azeotrope-like compositions with other compounds.

One example of this problem is in the manufacture of a fluoroolefin, tetrafluoroethylene ($CF_2=CF_2$; TFE). TFE is an important component in the manufacture of TFE fluorocarbon resins. TFE is usually manufactured by the pyrolysis reaction of monochlorodifluoromethane ($CHClF_2$; HCFC-22), which reaction can be represented by the equation:

$CF_2=CF_2 + 2HCl$

It is believed that in the above pyrolysis reaction, an intermediate, difluorocarbene, is formed which then dimerizes to form the desired TFE. However, difluorocarbene can also undergo an insertion reaction with TFE to form hexafluoropropylene ($CF_3-CF=CF_2$) and, thus, in this reaction, TFE is usually accompanied by some hexafluoropropylene. Hexafluoropropylene is a useful chemical and is important as a polymerizable fluoromonomer, as an intermediate for the preparation of fluorosurfactants and stable lubricants, and the like.

The above pyrolysis reaction of HCFC-22 can also be written as:

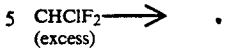

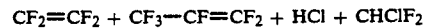

$CF_2=CF_2 + CF_3-CF=CF_2 + HCl + CHClF_2$

TFE and hydrogen chloride can be separated from the reaction mixture by distillation but the separation of hexafluoropropylene from HCFC-22 presents a problem since hexafluoropropylene and HCFC-22 form an azeotropic mixture which contains about 15 mol percent hexafluoropropylene and about 85 mol percent HCFC-22. As is well known, the separation of the components of an azeotropic or azeotrope-like mixture is difficult and often requires the addition of extraneous materials if a method such as extractive distillation is used. This usually creates additional problems of contamination and/or waste disposal.

It is therefore an object of the present invention to provide a process for the separation of the components of azeotropic or azeotrope-like mixtures containing only organic compounds at least one of which compounds is a halocarbon. Another object is to provide an economical and efficient process to accomplish the above objective.

Important advantages of the instant invention is that the separation is achieved without the addition of extraneous materials, without altering any of the components of the mixture and without creating additional waste disposal problems.

SUMMARY OF THE INVENTION

The present invention is a process for separating the components of an azeotropic or azeotrope-like mixture containing only organic compounds at least one of which compounds is a halocarbon comprising contacting such mixture with a semipermeable membrane to form at least one exit stream having an increased concentration of at least one component of the azeotropic or azeotrope-like mixture and at least one other exit stream having an increased concentration of at least one other component. Thereafter, the exit streams from the contacting step may be recycled for contact with the semipermeable membrane or further processed by conventional means to achieve additional separation and/or recovery of a desired component.

The invention is a process for separating and/or concentrating components of such azeotropic or azeotrope-like mixtures comprising providing a semipermeable membrane for separating the components of an azeotropic or azeotrope-like mixture containing only organic compounds of which at least one compound is a halocarbon, said semipermeable membrane having a feed side and a permeate side and having a selectivity for allowing the passage of at least one component of the azeotropic or azeotrope-like mixture relative to at least one other component of the azeotropic or azeotrope-like mixture;

contacting said azeotropic or azeotrope-like mixture with the feed side of the semipermeable membrane to form at least one exit stream having an increased concentration of at least one component of the azeotropic or azeotrope-like mixture and at least one other exit stream having a decreased concentration of the same component.

DETAILED DESCRIPTION OF THE INVENTION

In the context of the present invention, by halocarbon is meant a $C_1$ to $C_8$ halocarbon and includes chlorofluorocarbons, hydrogen-containing chlorofluorocarbons, perfluorocarbons, hydrogen-containing fluorinated hydrocarbons as well as fluorine-containing olefins.

As is generally known, an azeotrope is a mixture of two or more components wherein at constant pressure, the liquid phase and the vapor phase above it will have substantially identical compositions at the boiling point of the mixture. Thus, an azeotropic composition cannot normally be separated into its pure components by simple distillation. There are also mixtures which even though are not true azeotropes behave as though they were azeotropes, i.e., they distill with very little change in composition due to the closeness of the boiling points of the components in the mixture or due to some other reasons. In the present context, such mixtures are identified as azeotrope-like mixtures.

Among compositions which are azeotropic or azeotrope-like mixtures are the above-discussed mixture of hexafluoropropylene and monochlorodifluoromethane; other mixtures include but are not limited to:

perfluoropropane (FC-218) and monochlorodifluoromethane (HCFC-22);
1,1-dichloro-2,2,3,3,3-pentafluoropropane (HCFC-225ca) and 1,1-dichloro-1-fluoroethane (HCFC-141b);
1,1-dichloro-2,2,3,3,3-pentafluoropropane (HCFC-225ca) and 1,1,2-trichloro-1,2,2-trifluoroethane (CFC-113);
1,1-dichloro-2,2,3,3,3-pentafluoropropane (HCFC-225ca) and 1,1,2-trichloro-2,2-difluoroethane (HCFC-122);
1,1-dichloro-2,2,3,3,3-pentafluoropropane (HCFC-225ca) and 1,2-dichloro-1,1-difluoroethane (HCFC-132b);
1,1-dichloro-2,2,3,3,3-pentafluoropropane (HCFC-225ca) and dichloromethane;
1,2-dichloro-1,2,3,3,3-pentafluoropropane (HCFC-225ba) and and trans-1,2, dichloroethylene;
perfluoro-1,2-dimethyl cyclic butane (FC-C-51-12) and 1,1-dichloro-1-fluoroethane (HCFC-141b);
1,3-dichloro-1,1,2,2,3-pentafluoropropane (HCFC-225cb) and 1,1-dichloro-1-fluoroethane (HCFC-141b);
1,3-dichloro-1,1,2,2,3-pentafluoropropane (HCFC-225cb) and dichloromethane;
1,3-dichloro-1,1,2,2,3-pentafluoropropane (HCFC-225cb) and 1,1,2-trichloro-2,2-difluoroethane (HCFC-122);
1,3-dichloro-1,1,2,2,3-pentafluoropropane (HCFC-225cb) and 1,2-dichloro-1,1-difluoroethane (HCFC-132b);
1,3-dichloro-1,1,2,2,3-pentafluoropropane (HCFC-225cb) and 1,1,2-trichloro-1,2,2-trifluoroethane (CFC-113);
1-chloro-2,2,3,3-tetrafluoropropane (HCFC-244ca) and 1,1-dichloro-1-fluoroethane (HCFC-141b);
1-chloro-2,2,3,3-tetrafluoropropane (HCFC-244ca) and dichloromethane;
1-chloro-2,2,3,3-tetrafluoropropane (HCFC-244ca) and 1,2-dichloro-1,1-difluoroethane (HCFC-132b);
1-chloro-2,2,3,3-tetrafluoropropane (HCFC-244ca) and 1,1,2-trichloro-1,2,2-trifluoroethane (HCFC-113);
dichlorodifluoromethane (CFC-12) and monochlorodifluoromethane (HCFC-22);
dichlorodifluoromethane (CFC-12) and (HFC-134a).

As mentioned, separation of the components of an azeotropic or azeotrope-like mixture is not only difficult, but also usually costly. In addition, separation of the components in azeotropic or azeotrope-like mixtures when the desired component is present in very small amounts is especially difficult and may be impractical using methods such as extraction. The undesired component may be eliminated from the mixture by destructive means such as oxidation or hydrolysis but these methods are usually costly and contribute to the need to dispose of halide wastes.

In the present process, typically the difficult-to-separate azeotropic or azeotrope-like mixture is contacted with a selected semipermeable membrane to form two exit streams, each of which is enriched in at least one of the components of the original azeotropic mixture. The mixture which is contacted with the feed side of the semipermeable membrane does not have to be at the azeotropic or azeotrope-like concentration range, but merely capable of forming azeotropic or azeotrope-like mixtures. Subsequent treatment of the two exit streams obtained from the contacting step can provide the components of the original mixture in more purified forms. This is accomplished by utilizing the fact that the components form an azeotropic mixture and the two compositions obtained in the exit streams from the permeation separator can be distilled wherein the distillates will be the azeotropic or azeotrope-like composition which can be recycled to the inlet side of the permeation separator and the distillate bottoms may be essentially a purified component of the original azeotropic or azeotrope-like composition, or vice-versa.

The semipermeable membrane useful in the present invention can be any such device as is well known in the art and may be in any shape which has a feed side and a permeate side. Included in this description are semipermeable membranes which can be formed into films (with or without support), tubular devices, spiral wound devices, hollow fibers and the like. The ratio of permeation rates of at least one component of the difficult-to-separate azeotropic or azeotrope-like mixture (permeate) to that of at least one other component of the mixture (nonpermeate) should be greater than 1. Obviously, the higher the ratio, the more efficient will be the separation process.

The semipermeable membrane useful in the instant invention may be made from any material capable of preferentially passing one component relative to another component in a mixture which forms the azeotropic or azeotrope-like compositions of the present invention. Typically, the semipermeable membrane material is an elastomeric polymer made from natural rubbers, ceramics, polyisoprenes, polybutenes, polybutadienes, polyimides, aromatic-aliphatic polyamides, polyaramids, neoprenes, silicone elastomers and the like as is generally known in the art. Preferred semipermeable polymer membranes may be made of dimethylsilicone elastomers, polyimides and polyaramids. As in any permeation separation process, parameters which are usually considered as variables to enhance the separation process are the temperature, the pressure differential between the feed side of the membrane and the permeate side of the membrane, and the residence time of the feed stream on the feed side of the membrane and the residence time of the permeate on the permeate side of the membrane. In the instant invention, these parameters are not critical so long as the membrane material is not destructively affected and there is a difference in the permeation rate of one component compared to that of another component in the azeotropic or azeotrope-like mixture. Temperature can be any convenient temperature, usually from about −50 to 150 degrees C., the limitations being the temperatures wherein the membrane is affected adversely. Conveniently, the temperature range will be from about 0 to about 75 degrees C.

The pressure differential between the feed side of the membrane and the permeate side is preferably at least about one-tenth (0.1) atmosphere. The process may be operated at lesser pressure differential but the separation process will be slower. The pressure differential can be the result of higher pressure on the feed side of the semipermeable membrane or the result of reduced pressure on the permeate side of the membrane or a combination of both.

The process of the present invention may be illustrated by the separation of an azeotropic mixture of hexafluoropropylene (HFP) and monochlorodifluoromethane (HCFC-22). The azeotropic mixture of HFP and HCFC-22 contains about 23 weight percent HFP and about 77 weight percent HCFC-22. When this mixture is contacted with a permeation separator with, for example, dimethyl silicone elastomer as the semipermeable membrane, the permeate will be enriched in HCFC-22 and the non-permeate will be enriched in HFP. Ideally, the permeation separation will be complete such that the permeate will be pure HCFC-22 and the non-permeate will be pure HFP. Practically, however, the permeation separation and/or concentration process is a differential process, particularly when dealing with somewhat similar compositions as occur with halocarbon mixtures. Thus, the permeation process of the instant invention provides exit streams which are enriched in one or another of the mixture components but which are no longer at the concentration of the feed mixture.

In the present process, taking advantage of the partial separation as provided by the permeation separator and the fact that quantities of the azeotropic composition may still be present, further separation to provide essentially pure HFP and HCFC-22 is possible. Thus, the permeate stream can be distilled to take off the HFP/HCFC-22 azeotrope as the distillate, leaving behind purified HCFC-22 as distillate bottom. The azeotropic distillate can, thereafter, be recycled to the feed side of the permeation separator.

In a similar way, the non-permeate or the reject stream from the permeation separator can be distilled to provide an azeotropic mixture of HFP/HCFC-22 as the distillate which can be recycled to the inlet side of the permeation separator and the HFP in the non-permeate stream in excess of that amount required to form the azeotrope can be recovered as distillate bottom in a purity which may be sufficient for practical use.

The present process can be carried out as a batch process or as a continuous process. As described above, the present process is particularly amenable to operation as a continuous process, the azeotropic distillates being continuously recycled to the inlet side of the permeation separator and the purified HFP and HCFC-22 being continuously removed as distillation bottoms.

The efficiency of the present process depends upon the efficiency of the permeation separation portion of the process. The greater the enrichment process in the permeation separation, the more efficient is the whole separation process. Those skilled in the art can readily enhance the permeation separation process by adjusting temperature, pressure differentials, residence time and the like.

Other compounds, either azeotropic, non-azeotropic, organic or inorganic may be present during the contacting step of the instant invention.

The following examples are presented for illustrative purposes only and in no way are intented to limit the present process.

EXAMPLE 1

Permeation separation of hexafluoropropylene (HFP) and monochlorodifluoromethane (HCFC-22) was carried out using polycarbonate dimethylsilicone polymer (General Electric) membrane. The membrane was in the shape of a film and was supported in a circular device and claimped air-tight. The total surface of the membrane exposed to the mixtures of HFP and HCFC-22 was 0.104 sq. ft. (96.6 sq. cm.) and the clearance above the surface of the membrane was approximately 0.7 cm. A mixture of 15 mol percent (23.4 wt. percent) HFP and 85 mol percent (76.6 wt. percent) HCFC-22 was prepared in a cylinder. Appropriate valves were installed to control and monitor the flow of gases out of the cylinder. The cylinder was connected to the permeation device. The feed from the cylinder entered the permeation device via a 1/16" (0.16 cm.) stainless steel tube wherein the outlet of the stainless steel tube on the feed side of the permeation membrane was located on the perimeter of the circular device and a second similar 1/16" (0.16 cm.) stainless steel tube was located directly opposite the feed side so that the HFP/HCFC-22 mixture moved directly across the membrane surface and then exited the device via the second stainless steel tube.

The gas mixture exiting the permeation device was collected in an evacuated stainless steel cylinder and its composition determined by gas chromatography. Similarly, the permeate stream which passed through the membrane was collected in an evacuated stainless steel cylinder and its composition determined by gas chromatography.

The analyses of the streams are given in the following table.

| Separation of HFP/HCFC-22 | | | | |
|---|---|---|---|---|
| Feed Composition: | 23.4 wt. % HFP and 76.6 wt. % HCFC-22 | | | |
| Temp: | 20 degrees C. | | | |
| Pressures: | | | | |
| Feed Side: | atmospheric (760 mm Hg) | | | |
| Permeate Side: | 20" Hg Vac. (508 mm Hg vaccuum) | | | |
| Gas | Permeate (Wt %) | | Non-Permeate (Reject) (Wt %) | |
| Feed Rate* | HFP | HCFC-22 | HFP | HCFC-22 |
| 50 | 15.1 | 84.9 | 66.5 | 33.5 |
| 90 | 10.9 | 89.1 | 44.6 | 55.4 |
| 200 | 7.9 | 92.1 | 30.2 | 69.8 |
| 280 | 6.6 | 93.4 | 27.6 | 72.4 |
| 667 | 6.1 | 93.9 | 25.1 | 74.9 |

*gm./sq. ft/hr. (gm./sq. cm./sec.)

The above results show that HCFC-22 permeated considerably faster than HFP and that since both the permeate and the non-permeate are no longer azeotropic compositions of HFP and HCFC-22, purified HFP and HCFC-22 can be obtained readily from nonpermeate and permeate compositions respectively by distillations.

EXAMPLE 2

Separation of an azeotropic mixture of HFP and HCFC-22 which contains 23.4 wt. % of HFP and 76.6 wt. % HCFC-22 may be illustrated by this example.

Using a permeation membrane of polycarbonate dimethylsilicone copolymer elastomeric membrane (General Electric) having a surface area of approximately 2.24 sq. ft. (2081 sq. cm.), the above composition can be passed over the permeation membrane at the rate of about 203 gms./hr. at approximately 20 degrees C and atmospheric feed side pressure and a permeate side pressure of approximately 20" Hg vacuum (508 mm Hg vacuum).

The permeate stream can be about 129 gms./hr. of which about 115 gms./hr. (89 wt. %) is HCFC-22 and 14 gms./hr. (11 wt. %) is HFP. This permeate stream upon distillation provides about 61 gms./hr. of distillate and contains an azeotropic composition (76.6 wt. % HCFC-22 and 23.4 wt. % HFP) leaving behind about 69 gms./hr. of essentially pure HCFC-22.

The non-permeate or the reject stream can be about 74 gms./hr. and contains the composition 45.3 wt. % HFP and 54.7 wt. % HCFC-22. This non-permeate stream upon distillation provides about 53 gms./hr. of distillate which contains an azeotropic composition (76.6 wt. % HCFC-22 and 23.4 wt. % HFP) leaving behind about 21 gms./hr. of HFP in essentially purified form as distillation bottom.

The distillates from both the permeate stream and the non-permeate stream (total of about 113 gms./hr.) of azeotropic composition can be recycled to the inlet side of the permeation separator, which recycled materials in addition to about 90 g/hr. of additional azeotropic mixture constitutes 203 gms./hr. feed to the permeation separator.

This example illustrates that the present process can be operated in a continuous manner to provide purified HFP and purified HCFC-22 from their azeotropic mixture. The sizes of the permeation separator i.e. the surface area of the membrane available for permeation, the distillation columns and the attendant equipment necessary can be determined by those skilled in the art.

It can also be seen that the present process can be used advantageously with the process for manufacturing tetrafluoroethylene by the pyrolysis of HCFC-22 wherein the azeotropic mixture of HFP/HCFC-22 is produced and needs to be separated. Thus purified HCFC-22 produced from the permeate stream can be recycled to the manufacturing process, continuously if desired, and HFP recovered as valuable coproduct.

EXAMPLE 3

This example describes the use of a hollow-fiber permeator for the separation of hexafluoropropylene and monochlorodifluoromethane. The hollow-fiber membrane was made of a blend of polyimides and polyaramids, had a total surface area of 1.11 sq. ft. (1032 sq. cm.) and was exposed to an azeotrope-like mixture of HFP and HCFC-22. The results are shown in the following table:

| Separation of HFP/HCFC-22 | | | | |
|---|---|---|---|---|
| Feed Composition: | 22.2 wt. % HFP and 77.8 wt. % HCFC-22 | | | |
| Temp: | 20 degrees C. | | | |
| Pressures: | | | | |
| Feed Side: | 4.6 atmospheres (3,464 mm Hg) | | | |
| Permeate Side: | atmospheric pressure (760 mm Hg) | | | |
| Gas | Permeate (Wt %) | | Non-Permeate (Reject) (Wt %) | |
| Feed Rate* | HFP | HCFC-22 | HFP | HCFC-22 |
| 217 (6.5 × 10−5) | 1 | 99 | 99.8 | 0.2 |
| 393 (11.8 × 10−5) | 0.3 | 99.7 | 99.6 | 0.4 |
| 572 (17.1 × 10−5) | 0.3 | 99.7 | 99.5 | 0.5 |

*gm/sq. ft/hr. (gm./sq. cm./sec.)

The above results show that HCFC-22 permeated consistently faster than HFP since both the permeate and non-permeate are no longer azeotropic compositions of HFP and HCFC-22; purified HFP and HCFC-22 can be readily obtained from non-permeate and permeate compositions repectively by distillation. If the compositions as shown above are pure enough for direct use, then the additional distillation step becomes optional.

I claim:

1. A process for separating components of an azeotropic or azeotrope-like mixture containing only organic compounds at least one of which compounds is a halocarbon comprising contacting said azeotropic or azeotrope-like mixture with a semipermeable membrane to form at least one exit stream having an increased concentration of at least one component of the azeotropic or azeotrope-like mixture and at least one other exit stream having an increased concentration of at least one other component of the azeotropic or azeotrope-like mixture and, thereafter, recovering at least one exit stream and distilling the recovered exit stream to separate the component of the azeotropic or azeotrope-like mixture which is present in either increased or decreased concentration from any azeotropic or azeotrope-like mixture present in the recovered exit stream wherein concentration of at least one component of the azeotropic or azeotrope-like mixture in the exit stream is controlled by varying residence time of the azeotropic or azeotrope-like mixture on the feed side of the semipermeable membrane.

2. A process for separating components of an azeotropic or azeotrope-like mixture containing only organic compounds at least one of which compounds is a halocarbon comprising contacting said azeotropic or azeotrope-like mixture with a semipermeable membrane to form at least one exit stream having an increased concentration of at least one component of the azeotropic or azeotrope-like mixture and at least one other exit stream having an increased concentration of at least one other component of the azeotropic or azeotrope-like mixture and, thereafter, recovering at least one exit stream and distilling the recovered exit stream to separate the component of the azeotropic or azeotrope-like mixture which is present in either increased or decreased concentration from any azeotropic or azeotrope-like mixture present in the recovered exit stream wherein concentration of at least one component in the exit stream is controlled by varying residence time of the exit stream on the permeate side of the semipermeable membrane.

* * * * *